MS008138111B2

United States Patent
Wheeler et al.

(10) Patent No.: US 8,138,111 B2
(45) Date of Patent: Mar. 20, 2012

(54) TIME-DELAYED ACTIVATION OF ZEOLITE HEATING

(75) Inventors: Mark R. Wheeler, Rockaway, NJ (US); Milton E. McDonnell, Succasunna, NJ (US); Maria M. Higuera, Edgewater, NJ (US); Michael Jablon, Ramsey, NJ (US); Richard B. Heath, Morristown, NJ (US); Lee R. Mores, Hackettstown, NJ (US)

(73) Assignee: Honeywell International Inc., Morristown, NJ (US)

( * ) Notice: Subject to any disclaimer, the term of this patent is extended or adjusted under 35 U.S.C. 154(b) by 904 days.

(21) Appl. No.: 12/123,740

(22) Filed: May 20, 2008

(65) Prior Publication Data

US 2008/0305447 A1   Dec. 11, 2008

Related U.S. Application Data

(60) Provisional application No. 60/933,566, filed on Jun. 6, 2007.

(51) Int. Cl.
*B01J 29/06* (2006.01)
(52) U.S. Cl. .......................................... 502/60; 502/62
(58) Field of Classification Search .................. 502/60, 502/62; 432/29
See application file for complete search history.

(56) References Cited

U.S. PATENT DOCUMENTS

| 4,379,143 | A |   | 4/1983  | Sherry et al. |
| 5,254,283 | A |   | 10/1993 | Arnold et al. ............ 252/174.12 |
| 5,691,303 | A |   | 11/1997 | Pan et al. ........................... 512/4 |
| 5,876,755 | A |   | 3/1999  | Perring et al. ................. 424/489 |
| 5,965,264 | A | * | 10/1999 | Barenberg et al. ............ 428/402 |
| 6,180,549 | B1| * | 1/2001  | Mazany et al. ................. 502/64 |
| 6,790,814 | B1| * | 9/2004  | Marin et al. ................. 510/101 |
| 2004/0185023 | A1 |   | 9/2004 | Schnittger et al. ......... 424/70.14 |

FOREIGN PATENT DOCUMENTS

| JP | 60218307     | 11/1985 |
| JP | 06100411     | 4/1994  |
| JP | 2002020739   | 1/2002  |
| KR | 2001027020   | 4/2001  |
| KR | 20040056159  | 6/2004  |
| WO | WO2007075211 | 7/2007  |
| WO | WO2007087039 | 8/2007  |

OTHER PUBLICATIONS

Database WPI Week 200175, Thomson Scientific, London, GB 2001-653510 XP002493667.

* cited by examiner

*Primary Examiner* — Elizabeth Wood
(74) *Attorney, Agent, or Firm* — Ingrassia Fisher & Lorenz, PC

(57) ABSTRACT

The invention relates to zeolite particles which are at least partially coated with a coating that is capable of delaying the release of heat from the zeolite particles upon contact with water over time. The coating effectively at least partially blocks the pore structure of the zeolite particle from contact with water, thereby delaying contact between water and the zeolite, and prolonging the warming effect caused by such contact.

20 Claims, 1 Drawing Sheet

TIME-DELAYED ACTIVATION OF ZEOLITE HEATING

CROSS REFERENCE TO RELATED APPLICATION

This application claims the benefit of provisional application Ser. No. 60/933,566 filed Jun. 6, 2007, which is incorporated herein by reference.

BACKGROUND OF THE INVENTION

1. Field of the Invention

The present invention relates to the delayed generation of heat from zeolites upon contact with water. More particularly, the invention relates to coating zeolite particles such that the generation of heat from the zeolite particles is delayed when contacted with water.

2. Description of the Related Art

Zeolites are porous crystalline aluminosilicates, having fully cross-linked open framework structures made up of corner-sharing $SiO_4$ and $AlO_4$ tetrahedral groups. Zeolites belong to a class of minerals referred to generally as tectosilicates because their crystalline architecture is formed from silicon atoms in a tetrahedral, four-fold arrangement with oxygen atoms in a three dimensional lattice. The aluminosilicate structure is negatively charged and attracts the positive cations that reside within. Unlike most other tectosilicates, zeolites have large vacant spaces or cages in their structures that allow space for large cations such as sodium, potassium, barium and calcium and even relatively large molecules and cation groups such as water, ammonia, carbonate ions and nitrate ions. Zeolites are widely used as chemical sieves, odor absorbants, and dessicants.

Zeolites are known in the art for producing heat, almost instantaneously, upon hydration. Heat is generated as a result of adsorption of water within the structure of the zeolites. As long as zeolites stay dry, there will be no exothermic reaction. That is, zeolites undergo an exothermic reaction when transitioning from a dehydrated form to a hydrated form. A variety of anhydrous chemical formulations have been developed which contain such zeolites, so that the formulations may generate heat upon contact with water. Examples of such chemical formulations include a variety of personal care products such as lotions, cleansers, and other cosmetic formulations which generate heat when exposed to water, such as skin moisture, thereby producing a warming effect sensed by the skin. However, it is undesirable for this warming effect to occur too rapidly, become exhausted too quickly, or provide too much heat. With zeolites generating heat almost instantaneously upon contact with water, the warming effect of such cosmetic formulations is often intense and short-lived. A need therefore exists to delay the activation of the zeolite upon contact with water, such that heat is released continuously and gradually, and such that the warming effect lasts longer.

SUMMARY OF THE INVENTION

The present invention provides a solution to the existing problems in the art. The present invention relates to zeolite particles which are at least partially coated with a coating that is capable of delaying the release of heat from the zeolite particles upon contact with water over time. The coating effectively at least partially blocks the pore structure of the zeolite particle from contact with water, thereby delaying contact between water and the zeolite, and prolonging the warming effect caused by such contact.

The invention provides a time-delayed heat-release coated zeolite particle comprising a zeolite particle at least partially coated with a coating comprising a mixture of:
a) at least one water-soluble component which is at least partially soluble in water at temperatures of from about 15° C. to about 25° C.; and
b) at least one water-insoluble component which is substantially insoluble in water at temperatures of from about 15° C. to about 25° C.;
wherein the coating has a melting temperature of from about 45° C. to about 120° C., and wherein the coating is capable of dissolving in water at temperatures of from about 15° C. and 25° C. in an amount sufficient to at least partially expose the zeolite particle to the water.

The invention further provides a process for heating a fluid composition which comprises:
I) providing a fluid composition which comprises a plurality of time-delayed heat-release coated zeolite particles, each comprising a zeolite particle at least partially coated with a coating comprising a mixture of:
   a) at least one water-soluble component which is at least partially soluble in water at temperatures of from about 15° C. to about 25° C.; and
   b) at least one water-insoluble component which is substantially insoluble in water at temperatures of from about 15° C. to about 25° C.;
   wherein the coating has a melting temperature of from about 45° C. to about 120° C., and wherein the coating is capable of dissolving in water at temperatures of from about 15° C. and 25° C. in an amount sufficient to at least partially expose the zeolite particle to the water; and
II) contacting the fluid composition with water to thereby at least partially dissolve the coatings of the time-delayed heat-release coated zeolite particles, thus exposing the zeolite particles to the water such that the zeolite particles generate heat.

The invention further provides a process for forming time-delayed heat-release coated zeolite particles comprising:
I) forming a coating composition for coating zeolite particles, which comprises a mixture of:
   a) at least one water-soluble component which is at least partially soluble in water at temperatures of from about 15° C. to about 25° C.; and
   b) at least one water-insoluble component which is substantially insoluble in water at temperatures of from about 15° C. to about 25° C.;
II) heating the coating composition during or after step I, thereby forming a molten coating composition;
III) coating zeolite particles with the molten coating composition; and
IV) cooling the molten coating composition to thereby form time-delayed heat-release coated zeolite particles having a coating, which coating has a melting temperature of from about 45° C. to about 120° C., and which coating is capable of dissolving in water at temperatures of from about 15° C. and 25° C. in an amount sufficient for the zeolite particles to be at least partially exposed to the water.

The invention further provides a time-delayed heat-release coated zeolite particle comprising a zeolite particle partially coated with a water-insoluble coating, which coating comprises: a water-insoluble component comprising a crystalline or semicrystalline material having a glass transition temperature of about 40° C. or greater, and a melting point of about 150° C. or lower.

The invention further provides a process for heating a fluid composition which comprises:

I) providing a fluid composition which comprises a plurality of time-delayed heat-release coated zeolite particles, each comprising a zeolite particle partially coated with a water-insoluble coating which comprises a water-insoluble component comprising a crystalline or semicrystalline material having a glass transition temperature of about 40° C. or greater, and a melting point of about 150° C. or lower; and
II) contacting the fluid composition with water to thereby partially expose the zeolite particles to the water such that the zeolite particles generate heat.

The invention still further provides a process for forming time-delayed heat-release coated zeolite particles comprising:
I) forming a water-insoluble coating composition for coating zeolite particles, which comprises a water-insoluble component comprising a crystalline or semicrystalline material having a glass transition temperature of about 40° C. or greater, and a melting point of about 150° C. or lower;
II) heating the coating composition during or after step I, thereby forming a molten water-insoluble coating composition;
III) coating zeolite particles with the molten water-insoluble coating composition; and
IV) cooling the molten coating composition to thereby form time-delayed heat-release coated zeolite particles having a water-insoluble coating, which coating is sufficient to partially expose the zeolite particles to water.

DETAILED DESCRIPTION OF THE INVENTION

Figure 1:
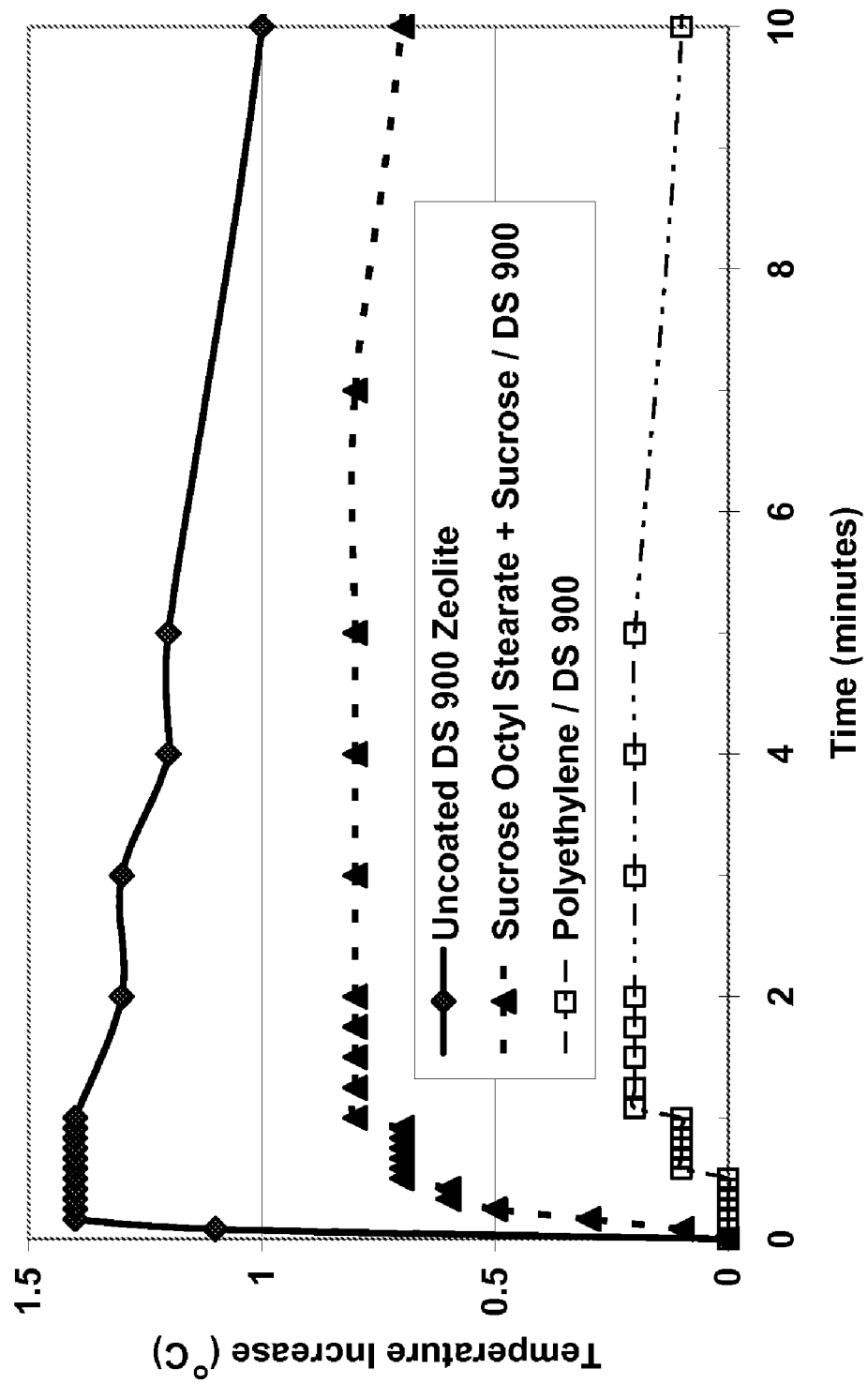
FIG. 1 shows a graphic representation of a temperature increase versus time profile of: uncoated zeolites, zeolites coated with a water-insoluble coating, and zeolites coated with a coating comprising a water-soluble component and a water-insoluble component.

The present invention provides time-delayed heat-release coated zeolite particles which generate a continuous, gradual heat upon contact with water.

The present invention provides a time-delayed heat-release coated zeolite particle, comprising a zeolite particle which is at least partially coated with a particular coating. In one aspect of this invention, a zeolite particle is partially coated with a water-insoluble coating formed from a coating composition comprising at least one water-insoluble component. In another aspect of the invention, the zeolite particle is at least partially coated with a coating formed from a coating composition comprising a mixture of at least one water-soluble component and at least one water-insoluble component, which coating is therefore at least partially water-soluble.

The term "coated zeolite particle" is defined herein as either a single coated zeolite particle, a plurality of individual coated zeolite particles, or coated clusters of zeolite particles, coated with the inventive coatings. The term "time-delayed heat-release" is defined herein as meaning that the coating on the zeolite particle at least partially blocks the zeolite structure from contact with water such that the underlying zeolite particle is gradually exposed to water over time, thus delaying the release of heat from the zeolite over time. In embodiments where the coating comprises a water-soluble component, the underlying zeolite particle is gradually exposed to water as the coating dissolves over time, thus allowing an influx of water into the zeolite at such a dissolved area of the coating. In embodiments where a water-insoluble coating is present, the underlying zeolite particle is gradually exposed to water via an uncoated area of the particle. That is, water contact with the zeolite structure is physically blocked in all areas except at an uncoated area, where water influx occurs.

It is preferred that this delay in the exposure of the zeolite particle to water is such that it allows heat to be generated from the zeolite particle gradually, thereby prolonging a warming effect caused by the zeolite's heat generation. In this invention, the terms "generation" and "release" of heat are used interchangeably, and refer to the release of heat from within the zeolite.

The water-insoluble component of the coatings of the present invention is substantially insoluble, and preferably completely insoluble, in water at temperatures of from about 15° C. to about 25° C. The term "substantially insoluble" is defined herein as being at least about 99% insoluble in an equal weight of water at these temperatures. The water-insoluble component serves to at least partially inhibit or block the exposure of the crystalline lattice structure of the zeolite particle to water. Examples of suitable water-insoluble components nonexclusively include saccharide esters, esterified polyols, waxes, or di- or tri-block copolymers of ethylene oxide and propylene oxide, preferably having a hydrophilic lipophilic balance (HLB) of from about 0 to about 7, and containing sufficient propylene oxide chains to behave as a water insoluble material as described herein, and combinations thereof. Suitable saccharide esters nonexclusively include sucrose octyl stearate, sucrose stearate, and sucrose distearate. Suitable esterified polyols nonexclusively include polyglyceride fatty acid esters. Suitable waxes nonexclusively include animal, vegetable, mineral, petroleum or synthetic waxes. One preferred water-insoluble component comprises sucrose octyl stearate.

In embodiments wherein a water-insoluble coating is formed, the water-insoluble component comprises a crystalline or semicrystalline material having a glass transition temperature of about 40° C. or greater, and a melting point of about 150° C. or lower. A melting point of 150° C. enables the coating material to applied as a liquid, as described below. To provide only partial coverage of the zeolite with a coating applied as a liquid, the coating is preferably cooled to a solid state, and cracked or otherwise broken such that the particle is only partially coated, and to provide areas where an influx of water into the zeolite structure is possible. In practice, this is preferably achieved by a crystalline or semi-crystalline coating. In addition, in certain embodiments it is preferred that the glass transition temperature of the coating is high enough so that it will crack or otherwise break away. This is enabled by a glass transition temperature of 40° C. or greater. In such embodiments where the zeolite particles are partially coated with a water-insoluble coating, preferred water-insoluble components comprise an esterified polyol, a wax, or di- or tri-block copolymers of ethylene oxide and propylene oxide, preferably having a hydrophilic lipophilic balance (HLB) of from about 0 to about 7, and containing sufficient propylene oxide chains to behave as a water insoluble material as described herein, or combinations thereof. A preferred esterified polyol for such an embodiment has a linear alkane chain of 12 to 22 carbon atoms. In addition, in certain embodiments it is preferred that the coating has a hardness of about 5 dmm or less, as specified by ASTM method D1321-04. That is, it may be preferable for the coating to have a sufficient hardness such that it will crack or otherwise break away.

In embodiments where a water-soluble component is present in the coating, the water-soluble component is at least partially soluble in water at temperatures of from about 15° C. to about 25° C. The water-soluble component makes it possible for at least a portion of the coating to dissolve in water, in an amount sufficient to at least partially expose the crystalline lattice structure of the zeolite particle to the water. Examples of suitable water-soluble components nonexclusively include sucrose, glucose such as D-glucose, fructose, amylose, amylopectin, polyethylene glycols such as PEG-80 and PEG-150, anionic mild surfactants such as taurates and glutamates, fatty esters of ethylene glycol, mono- and/or divalent salts of an alkali or alkaline earth metal and a halide or nonmetal oxide such as, but not limited to, sodium chloride, magnesium chloride, lithium sulfate, calcium carbonate, and magnesium sulfate, or di- or tri-block copolymers of ethylene oxide and propylene oxide, preferably having a hydrophilic lipophilic balance (HLB) of greater than about 7, and containing sufficient ethylene oxide chains to behave as a water soluble material as described herein, or combinations thereof. A preferred water-soluble component comprises sucrose.

The zeolite particles used in this invention serve to generate and release heat upon contact with water. Examples of suitable zeolites for the present invention nonexclusively include those of the zeolite "Type A family." Commonly referred to as "Zeolite A," these materials include synthetic zeolites which exhibit the LTA (Linde Type A) structure. They may be defined as having a 3-dimensional pore structure with rows of pores running perpendicular to each other in the x, y, and z planes, and are made of secondary building units 4, 6, 8, and 4-4. Their pore diameters may be defined by an eight member oxygen ring and is small at about 4.2 Å. This leads into a larger cavity of a minimum free diameter of about 11.4 Å. Their cavities may be surrounded by eight sodalite cages (truncated octahedra) connected by their square faces in a cubic structure. Type A zeolites thermally decompose at about 700° C. Examples of suitable Type A zeolites for this invention nonexclusively include sodium Type A zeolites, sodium potassium Type A zeolites, and calcium Type A zeolites, otherwise known as Type 3A, 4A and 5A zeolites, and/or combinations thereof. One preferred zeolite comprises a sodium-potassium Type A zeolite, such as Asensa™ DS 900, which is commercially available from Honeywell International, Inc. of Morristown, N.J. The zeolite particles preferably have a particle size ranging from about 0.1 μm to about 100 μm, more preferably from about 5 μm to about 25 μm, and most preferably from about 6 μm to about 10 μm. It should further be noted that other conventional heat producing materials may also be coated with the coating systems described herein. Examples of such alternate heat producing chemicals nonexclusively include magnesium sulfate and calcium carbonate.

The coatings of the present invention preferably have a thickness of from about 0.1 μm to 10 μm, more preferably from about 0.5 μm to about 5 μm, and most preferably from about 1 μm to about 2 μm. Variations in thickness may result in exposure of the zeolite at different rates, depending on the solubility of the coating. In certain embodiments, the coating has a substantially uniform thickness around the zeolite particles, preferably such that the thickness does not vary by more than about 10% of the mean thickness. In other embodiments, the coating has a non-uniform, variable thickness around the zeolite particles. Furthermore, in certain embodiments, the zeolite particles are substantially entirely coated with the coating, whereby at least about 99% of the zeolite particle is coated. In other embodiments, the zeolite particles are less than entirely coated with the coating. For instance, where the coating comprises a water-soluble component, the coated zeolite particles are at least partially coated, and preferably substantially entirely coated, with the coating. In contrast, where the coating is water-insoluble, the coated zeolite particles are partially coated, that is, they are less than entirely coated with the coating. In one embodiment, where the zeolite particles are partially coated with a water-insoluble coating, the particles are each at least about 80% coated. In another embodiment, where the zeolite particles are partially coated with a water-insoluble coating, the particles are each at least about 90% coated.

By "exposing" the zeolite particles to water, or "contacting" the zeolite particles with water, it is meant that the crystalline lattice structure of the zeolite particle is contacted with the water, thereby releasing a portion of heat from within the zeolite. It is preferred that this heat is released gradually over time. In those embodiments where the coating includes a water-soluble component, the coating gradually dissolves over time, such that water molecules are able to contact the zeolite's crystalline lattice structure over time, and heat is released gradually by the zeolite particle. In those embodiments where the coating is water-insoluble, the zeolite particle may be partially coated such that portions the outer surface of the zeolite are blocked by the coating, and water may only enter into and contact zeolite structure at areas which are not coated, or a portion of the coating may be partially removed or broken. In either embodiment, the coating is effective to delay the generating of heat by the zeolite particle, by blocking the particle's exposure to water.

A desired feature of the inventive time-delayed heat-release coated zeolite particles is that they provide a sustained heat release over time. It is preferred that these time-delayed heat-release coated zeolite particles generate heat gradually over a timeframe of about 1 to about 15 minutes. In further embodiments of this invention, the time-delayed heat-release coated zeolite particles generate heat over a timeframe of about 1 to about 30 minutes. In still further embodiments, the time-delayed heat-release coated zeolite particles generate heat over a timeframe of about 1 to about 60 minutes. Longer heating times may also be desired. Variations in the components of the coating composition, particularly in the water-insoluble components and/or the water-soluble components and their amounts, will result in exposure of the zeolite at different rates.

The coating preferably has a melting temperature of from about 45° C. to about 120° C., more preferably from about 50° C. to about 100° C., and most preferably from about 55° C. to about 90° C. In a further preferred embodiment, the coating has a melting temperature of from about 55° C. to about 65° C. It is preferred that the coating is a solid or liquid at room temperature. The term "solid" is defined herein as meaning that the coating is present in a solid physical state at room temperature. The term "liquid" is defined herein as meaning that the coating is present in a liquid physical state at room temperature. The coating is also preferably thermally stable at temperatures of at least about 10° C. higher than its melting temperature. By thermally stable, it is meant that the coating does not thermally degrade at the stated temperature. That is, at the stated temperature, it is preferable that the solubility of the coating does not substantially change or degrade in such a way that it would affect the rate at which the coating dissolves in water. In a preferred embodiment, the coating composition is also preferably thermally stable at temperatures of up to about 130° C.

The invention further provides a process for forming the present time-delayed release coated zeolite particles. This process first comprises the step of formulating a coating composition. The coating compositions according to this invention may be formulated to result in either a water-insoluble coating, or an at least partially water-soluble coating, that is, a coating which contains a water-soluble component. A coating composition suitable for formulating a water-insoluble coating comprises a water-insoluble component comprising a crystalline or semicrystalline material having a glass transition temperature of about 40° C. or greater, and a melting point of about 150° C. or lower. A coating composition suitable for formulating an at least partially water-soluble coating comprises a mixture of:

a) at least one water-soluble component which is at least partially soluble in water at temperatures of from about 15° C. to about 25° C.; and b) at least one water-insoluble component which is substantially insoluble in water at temperatures of from about 15° C. to about 25° C.

During or after formation of the coating composition, the composition is heated to form a molten coating composition, that is, the coating composition is present in a melted, fluid state. Zeolite particles, as described above, are then coated with the molten coating composition. The molten coating composition is then cooled to form time-delayed heat-release coated zeolite particles having a coating thereon. The cooled coating may be a complete coating or a partial coating.

In one embodiment, the coating composition is simultaneously formed and heated. In another embodiment, the coating composition is heated after it is formed. In another embodiment, the coating composition is simultaneously formed, heated, and coated onto the zeolite particles.

Coating the molten coating composition onto the zeolite particles may be done using any conventionally known coating techniques. In one embodiment, the zeolite particles are coated by dipping. In another embodiment, the zeolite particles are spray coated. In other embodiments, the zeolite particles are coated in a fluidized bed reactor, or a batch reactor.

In one embodiment of the invention, the molten coating composition is combined with the zeolite particles, such as by mixing, to form a fluid zeolite composite. The fluid zeolite composite is then cooled to form a zeolite composite. This zeolite composite is then separated into coated zeolite particles. This separation may be conducted via any suitable conventional method such as grinding, blending, milling, fracturing, attrition or the like. The separated coated zeolite particles may be completely coated or partially coated with a desired coating. In one embodiment, the separation step removes portions of the coating from the zeolite, resulting in partially coated zeolite particles.

The coated zeolite particles of the present invention may be useful in a variety of commercial and industrial applications, including cosmetic, agricultural, environmental, construction, medical, automotive, and fuel applications, among others. In preferred embodiments of this invention, a variety of carrier compositions are formulated which comprise a plurality of the time-delayed heat-release coated zeolite particles described above. Such carrier compositions are heated by contacting them with water to thereby expose the zeolite particles to the water such that the zeolite particles release heat over time. Carrier compositions containing the inventive particles may be considered "self-heating," since they generate their own heat upon contact with water. Particularly suitable carrier compositions include anhydrous carrier compositions, including anhydrous fluids. Examples of cosmetically acceptable carrier compositions for use in accordance with the present invention nonexclusively include lotion compositions, cleanser compositions, facial mask compositions, make-up compositions, and the like. Such carrier compositions may comprise other conventional heat producing materials, as stated above, such as magnesium sulfate, calcium carbonate, and the like.

In one embodiment of this invention, a self-heating facial cleanser composition is formed. A plurality of the time-delayed heat-release coated zeolite particles, as described above, are mixed with suitable cosmetic ingredients to form a facial cleanser composition capable of generating a gradual heating upon contact with water, such as skin moisture. The self-heating facial cleanser composition preferably comprises from about 10 to about 90 wt. % of the time-delayed heat-release coated zeolite particles, more preferably from about 12 to about 50 wt. %, and most preferably from about 15 to about 25 wt. %. In one particular embodiment, shown in Example 6, a self-heating facial cleanser composition includes coated zeolite particles comprising Honeywell's Asensa™ DS 901 zeolite particles which are coated with a coating comprising sucrose and sucrose octyl stearate. The self-heating facial cleanser composition further comprises a surfactant such as sodium lauryl sulfoacetate. The composition may optionally further comprise additional components such as glycerin, salts, oils, fragrances, colorants, moisturizers, exfoliants, and the like. In one particular embodiment, shown in Example 6, a self-heating facial cleanser composition includes an exfoliant comprising Honeywell's Asensa™ SC 210.

The self-heating facial cleanser composition is preferably applied to a user's face, where it comes into contact with skin moisture and optional additional water, to thereby produce a warming effect. This warming effect preferably lasts for a time of from about 1 to about 15 minutes, more preferably from about 1 to about 30 minutes, and most preferably from about 1 to about 60 minutes, or greater, as described above. A further embodiment comprises a cosmetic cloth which has been impregnated with a cosmetically acceptable carrier composition, such as the self-heating facial cleanser composition as described above.

The zeolite coatings of the present invention in a carrier composition provide a significant delay the release of heat from the zeolite via water contact such that the time to reach maximum temperature of the carrier composition is delayed relative to an uncoated zeolite. It is further preferred that the inventive zeolite coatings additionally provides a significant rise in temperature of the carrier composition, as compared to the same quantity of uncoated zeolite. The most beneficial results are achieved by the combination of a significant delay in reaching maximum temperature, as well as a significant rise in temperature, as compared to an uncoated zeolite.

Examples 1-5 below show that the inventive coatings are capable of providing a significant time delay, and in certain cases additionally a significant rise in temperature. The coated zeolites having the inventive invention should delay the time at which the maximum temperature (Tmax) of a carrier composition is reached by at least about 20 seconds above that of a comparative uncoated zeolite, to be considered significant and effective. A delay in the time for to reach maximum temperature of about 30 seconds is preferred. A significant temperature increase is considered to be a temperature change that may be detected by human skin within the time frame of the experiment. Therefore, a significant temperature rise according to this invention is considered to be an increase in maximum temperature (ΔTmax) of at least 0.4° C. above that of the ambient starting temperature of the carrier composition. Larger temperature increases can be obtained from the coated zeolite by increasing the amount of coated zeolite or reducing the amount of water present.

The following non-limiting examples serve to illustrate the invention. It will be appreciated that variations in proportions and alternatives in elements of the components of the invention will be apparent to those skilled in the art and are within the scope of the present invention.

The data relating to Examples 1-5 is shown in Table 1.

TABLE 1

Effects of Coating Zeolites on Heating Rates.

| System | Time to reach $T_{MAX}$ (Seconds) | $\Delta T_{MAX}$ (° C.) over ambient temp |
|---|---|---|
| Reference zeolite: No Coating | 7 | 1.4 |
| Zeolite/sucrose octyl stearate/sucrose (ratio = 10:4:4) | 60 | 0.8 |
| Zeolite/sucrose octyl stearate (ratio = 5:2) | 25 | 0.4 |
| Zeolite + PEG-8000 (ratio = 5:2) | 10 | 1.4 |
| Zeolite + PE-homopolymer (ratio = 1:3) | 75 | 0.2 |

It is noted that the thermocouple used for measuring the above temperatures may have a resolution of ±0.1° C.

EXAMPLE 1

Comparative

An uncoated Type A zeolite (Asensa™ DS 900) was provided, in powder form.

Approximately 195 g of water at ambient temperature was charged into an insulated vessel (10 oz Thermos™ flask). The water was agitated using a twin-blade paddle stirrer (IKA Works RW 11; R1001 paddle stirring element). The temperature of the water is measured by a thermocouple suspended in the fluid (VWR Flip-Stick). Approximately 6 g of the uncoated zeolite powder was rapidly added to the water, and the temperature of the resulting mixture was recorded for up to 10 minutes. Maximum temperature (Tmax) of the water was reached in 7 seconds, and the change in maximum temperature (ΔTmax), was measured at 1.4° C. above the ambient starting temperature of the water.

A temperature increase versus time profile of the behavior of the uncoated DS 900 zeolite in water is shown in FIG. 1. The data of FIG. 1 shows that the uncoated zeolite generates heat rapidly and intensely upon initial contact with water, with its maximum temperature being achieved upon this initial contact, followed by a rapid decrease in temperature over time.

EXAMPLE 2

A mixture of a sodium-potassium Type A zeolite (Honeywell Asensa™ DS 900), sucrose octyl stearate, and sucrose in a ratio of 10:4:4 was prepared by melting the sucrose stearate and sucrose in a stainless steel Waring blender, and adding the zeolite to the molten material. As the mixture cooled, it was blended at high speed to make a fine powder of coated zeolite particles.

Approximately 195 g of water at ambient temperature was charged into a 10 oz insulated flask. The water was agitated using a twin-blade paddle stirrer (IKA Works RW 11; R1001 paddle stirring element). The temperature of the water is measured by a thermocouple suspended in the fluid (VWR Flip-Stick). Approximately 11 g of the coated zeolite sample, which provides the equivalent of approximately 6 g of uncoated zeolite, was rapidly added to the water, and the temperature of the resulting mixture was recorded for up to 10 minutes. Maximum temperature (Tmax) of the water was reached in 60 seconds, and the change in maximum temperature (ΔTmax), was measured at 0.8° C. above the ambient starting temperature of the water. These results therefore show a significant delay in reaching maximum temperature as compared to the uncoated zeolite of Example 1, and a significant temperature rise as compared to Example 1.

A temperature increase versus time profile of the behavior of the sucrose octyl stearate and sucrose coated Asensa™ DS 900 zeolite in water is shown in FIG. 1. The data of FIG. 1 shows that the inventive coatings delay the reaching of maximum temperature, and control the intensity of the initial heating temperature upon first contact with water, as compared to the uncoated zeolite particles. The data of FIG. 1 shows that the heat generation of the coated zeolite initially increases over time, and thereafter produces a steady, even heating. This shows a clear improvement over the uncoated zeolite particles.

EXAMPLE 3

Sodium-potassium Type A zeolite particles (Honeywell Asensa™ DS 900) were coated with sucrose octyl stearate in a ratio of 5:2 using the method described above in Example 2, and 8 g of the coated particles, which provides the equivalent of approximately 6 g of uncoated zeolite, were added to 195 ml of water, as described above. Maximum temperature (Tmax) of the water was reached in 25 seconds, and the change in maximum temperature (ΔTmax), was measured at 0.4° C. above the ambient starting temperature of the water. These results showed a significant delay in reaching maximum temperature as compared to the uncoated zeolite of Example 1, and a significant temperature rise as compared to Example 1.

EXAMPLE 4

Comparative

Sodium-potassium Type A zeolite particles (Honeywell Asensa™ DS 900) were coated with PEG-8000 in a ratio of 5:2 using the method described above in Example 2, and 8 g of the coated particles, which provides the equivalent of approximately 6 g of uncoated zeolite, were added to 195 ml of water, as described above. Maximum temperature (Tmax) of the water was reached in 10 seconds, and the change in maximum temperature (ΔTmax), was measured at 1.4° C. above the ambient starting temperature of the water. These results showed no significant delay in reaching maximum temperature as compared to the uncoated zeolite of Example 1, but showed a significant temperature rise as compared to Example 1. This comparative coating does not provide the benefits of the inventive coatings.

EXAMPLE 5

Sodium-potassium Type A zeolite particles (Honeywell Asensa™ DS 900) were coated with polyethylene homopolymer in a ratio of 1:3 using the method described above in Example 2, and 18 g of the coated particles, which provided the equivalent of approximately 4.5 g of uncoated zeolite, were added to 195 ml of water, as described above. Maximum temperature (Tmax) of the water was reached in 30 seconds, and the change in maximum temperature (ΔTmax), was measured at 0.2° C. above the ambient starting temperature of the water. These results showed a significant delay in reaching maximum temperature as compared to the uncoated zeolite of Example 1, and a small temperature rise as compared to Example 1.

A temperature increase versus time profile of the behavior of polyethylene coated Asensa™ DS 900 zeolite particles in water is shown in FIG. 1. It is shown in FIG. 1 that the inventive coatings delay the reaching of maximum temperature, and control the intensity of the initial heating temperature upon first contact with water, as compared to uncoated zeolite particles. FIG. 1 also shows that the heat generation of the coated zeolite initially increases over time, and thereafter produces a steady, even heating. This shows a clear differentiation from the uncoated zeolite particles

EXAMPLE 6

A mixture of Asensa™ DS 901 zeolite, sucrose octyl stearate, and sucrose in a ratio of 10:4:4 is prepared by melting the sucrose stearate and sucrose in a stainless steel Waring blender, and adding the zeolite to the molten material. As the mixture cooled, it is blended at high speed to make a fine powder of coated zeolite particles.

A self-heating facial cleanser composition is formulated using the following materials:

| Ingredient: | % by wt | Batch size (500 parts) |
|---|---|---|
| PEG-200 castor oil | 53.60 | 281.5 |
| Glycerin (99%) | 10.00 | 50.00 |
| coated Asensa ™ DS 901 particles | 15.00 | 75.00 |
| Sodium lauryl sulfoacetate | 17.50 | 87.50 |
| Asensa ™ SC 210 | 1.00 | 5.00 |
| Sea salt | 0.20 | 1.00 |

The PEG-200 castor oil and glycerin are combined in a vessel. Next, the coated Asensa™ DS 901 particles, sodium lauryl sulfoacetate, and Asensa™ SC 210 exfoliant are individually added to the vessel and mixed in thoroughly. Finally, 1 part of sea salt is added, and the combination is mixed thoroughly. The result is a self-heating facial cleanser composition containing the inventive coated zeolite particles.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A time-delayed heat-release coated zeolite particle comprising a zeolite particle at least partially coated with a coating comprising a mixture of:
   a) at least one water-soluble component which is at least partially soluble in water at temperatures of from about 15° C. to about 25° C.; and
   b) at least one water-insoluble component which is substantially insoluble in water at temperatures of from about 15° C. to about 25° C.;
   wherein the coating has a melting temperature of from about 45° C. to about 120° C., and wherein the coating is capable of dissolving in water at temperatures of from about 15° C. and 25° C. in an amount sufficient to at least partially expose the zeolite particle to the water.

2. The time-delayed heat-release coated zeolite particle of claim 1, wherein the zeolite particle is coated such that the coating becomes at least partially dissolved at a time of from about 1 minute to about 60 minutes upon contact with water.

3. The time-delayed heat-release coated zeolite particle of claim 1 wherein the coating composition is thermally stable at temperatures of up to about 130° C.

4. The time-delayed heat-release coated zeolite particle of claim 1 wherein the zeolite particle comprises a 3A zeolite, a 4A zeolite, a 5A zeolite or combinations thereof.

5. The time-delayed heat-release coated zeolite particle of claim 1 wherein the water-soluble component comprises sucrose, glucose, fructose, amylose, amylopectin, polyethylene glycol, taurates, glutamates, fatty esters of ethylene glycol, mono- and/or divalent salts of an alkali or alkaline earth metal and a halide or nonmetal oxide, di- or tri-block copolymers of ethylene oxide and propylene oxide, or combinations thereof.

6. The time-delayed heat-release coated zeolite particle of claim 1 wherein the water-soluble component comprises sucrose.

7. The time-delayed heat-release coated zeolite particle of claim 1 wherein the water-insoluble component comprises a saccharide ester, an esterified polyol, a wax, or combinations thereof.

8. The time-delayed heat-release coated zeolite particle of claim 1 wherein the water-insoluble component comprises sucrose octyl stearate.

9. The time-delayed heat-release coated zeolite particle of claim 1 wherein the zeolite particle is substantially entirely coated with the coating composition.

10. The time-delayed heat-release coated zeolite particle of claim 1 wherein the zeolite particle is less than entirely coated with the coating composition.

11. The time-delayed heat-release coated zeolite particle of claim 1 wherein the coating composition has a thickness of from about 0.1 μm to about 10 μm.

12. The time-delayed heat-release coated zeolite particle of claim 1 wherein the at least one water-insoluble component comprises a crystalline or semicrystalline material having a glass transition temperature of no less than about 40° C. and a melting point of about 150° C. or lower.

13. The time-delayed heat-release coated zeolite particle of claim 1 wherein the time-delayed heat-release coated zeolite particle has a particle size in the range of from about 0.1 μm to about 100 μm.

14. The time-delayed heat-release coated zeolite particle of claim 13 wherein the time-delayed heat-release coated zeolite particle has a particle size in the range of from about 5 μm to about 25 μm.

15. The time-delayed heat-release coated zeolite particle of claim 14 wherein the time-delayed heat-release coated zeolite particle has a particle size in the range of from about 6 μm to about 10 μm.

16. The time-delayed heat-release coated zeolite particle of claim 11 wherein the coating composition has a thickness of from about 0.5 μm to about 5 μm.

17. The time-delayed heat-release coated zeolite particle of claim 16 wherein the coating composition has a thickness of from about 1 μm to about 2 μm.

18. The time-delayed heat-release coated zeolite particle of claim 1 wherein the coating has a melting temperature of from about 50° C. to about 100° C.

19. The time-delayed heat-release coated zeolite particle of claim 1 wherein the coating has a melting temperature of from about 55° C. to about 90° C.

20. The time-delayed heat-release coated zeolite particle of claim 1 wherein the coating has a melting temperature of from about 55° C. to about 65° C.

* * * * *